United States Patent [19]

Kaplan et al.

[11] 4,302,446

[45] Nov. 24, 1981

[54] PHARMACEUTICAL COMPOSITIONS

[75] Inventors: Murray A. Kaplan, Syracuse; Alphonse P. Granatek, Baldwinsville, both of N.Y.

[73] Assignee: Bristol-Myers Company, New York, N.Y.

[21] Appl. No.: 81,301

[22] Filed: Oct. 2, 1979

[51] Int. Cl.³ .................. A01N 11/00; C01F 15/00
[52] U.S. Cl. .................. 424/131; 423/409; 260/429 R
[58] Field of Search ............ 260/429 R; 423/409; 424/131

[56] References Cited
PUBLICATIONS

Greene et al., American Journal of Hospital Pharmacy 36, 38-43, (1979).
Rozencweig et al., Annals of Internal Medicine, 86, 803-812, (1977).
Talley et al., Cancer Chemotherapy Reports, 57, 465-471, (1973).
Rossof et al., Cancer, 30 1451-1456, (1972).
Rosenberg et al., Nature 205 698-699, (1965).
Rosenberg et al., Nature 222 385-386, (1966).
Handelsman et al., Clinical Brochure, Cis Platinum (II), Diamminedichlori de National Cancer Inst., pp. 31 & 32, (1974).

Primary Examiner—Helen M. S. Sneed
Attorney, Agent, or Firm—Richard R. Lloyd

[57] ABSTRACT

A stable, microcrystalline form of cisplatin, a process for its preparation, and stable, sterile dry-mix formulations thereof which are more rapidly reconstituted with sterile water to produce solutions suitable for intravenous administration to man than are similar formulations containing "regular" cisplatin. The microcrystalline cisplatin and dry-mix formulations thereof are prepared without the use of lyophilization.

15 Claims, No Drawings

PHARMACEUTICAL COMPOSITIONS

BACKGROUND AND PRIOR ART

This invention relates to a stable, rapidly soluble, microcrystalline form of cisplatin, and to dry-mix formulations thereof, which, after reconstitution with sterile water, are used by injection in the chemotherapy of cancer.

The platinum compounds are a unique group of compounds in the antineoplastic group of agents. They were first noted to have an antibiotic effect by Rosenberg and his colleagues in 1965 [Rosenberg, B. et. al., Nature (London), 205, 698–699 (1965)] and subsequently found by Rosenberg and his colleagues to be potent antitumor agents in animals [Rosenberg, B. et. al., Nature (London), 222, 385–386 (1969)].

Structurally they represent a complex formed by a central atom of platinum and surrounded by various arrangements of chlorine atoms or ammonia groups in either a cis or trans planar relationship. Two of the more commonly studied platinum compounds are diagrammed below:

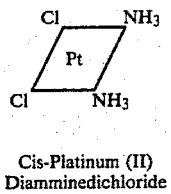
Cis-Platinum (II)
Diamminedichloride

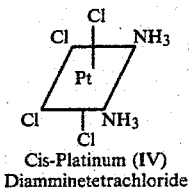
Cis-Platinum (IV)
Diamminetetrachloride

As can be seen, the compound cis-platinum (II) diamminedichloride has all its chloro and amino groups in a single plane. This compound, now known by the United States Adopted Name (USAN) cisplatin, has been synthesized according to the following reaction:

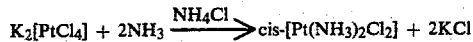

[see Kauffman, G. B. et al., in *Inorganic Synthesis*, J. Kleinberg (Ed.), pages 239–245, McGraw-Hill Book Co., Inc., New York, 1963].

Breusova-Baidala, Y. G. et al., in *Akademia Nauk SSSR*, No. 6, pp. 1167–1169 (June 1974), discuss the slow isomerization of cis-platinum (II) diamminedichloride in aqueous solution to the trans form.

Reishus, J. W. and Martin, D. S., in *Journal of The American Chemical Society*, 83, 2457–2462 (1961), describe the acid hydrolysis of cisplatin at 25° C. and 35° C. These studies were conducted in aqueous solutions at concentrations of $1.5 \times 10^{-3}$ M, $2.5 \times 10^{-3}$ M and $5.0 \times 10^{-3}$ M, which correspond to 0.45, 0.75 and 1.5 mg./ml., respectively. The authors state that there was some ambiguity in locating the origin (i.e. "zero point") for the hydrolysis curves because the samples required from 10 to 30 minutes to dissolve completely even at those low concentrations.

Rozencweig, M. et al., in *Annals of Internal Medicine*, 86, 803–812 (1977), review the results of various preclinical and clinical investigations of the use of cisplatin in experimental tumors in animals as well as various types of human tumors. They point out that the investigational drug, available to qualified investigators through the Investigational Drug Branch and the Cancer Therapy Evaluation Program of the National Cancer Institute, was supplied as a white lyophilized powder in vials containing 10 mg. of cisplatin, 90 mg. of sodium chloride, 100 mg. of mannitol (U.S.P.) and hydrochloric acid for pH adjustment. When reconstituted with 10 ml. of sterile water for injection (U.S.P.), each ml. of the resulting solution would contain 1 mg. of cisplatin, 10 mg. of mannitol and 9 mg. of NaCl.

Talley, R. W. et al., in *Cancer Chemotherapy Reports*, 57, 465–471 (1973), describe the results of their Phase I clinical study of the use of cisplatin in the treatment of 65 human patients with a wide variety of neoplasms. As in the preceding publication, the drug was supplied to them by the National Cancer Institute in vials containing 10 mg. of cisplatin, 90 mg. sodium chloride and 100 mg. of mannitol, for reconstitution with 10 ml. of sterile water.

Rossof, A. H. et al., in *Cancer*, 30, 1451–1456 (1972), describe the results of their use of cisplatin in the treatment of 31 human patients with a variety of tumor types. They state that the drug supplied by the National Cancer Institute was manufactured by Ben Venue Laboratories, Inc. and contained, per vial, 10 mg. of cisplatin, 10 mg. (sic) of mannitol and 9 mg. (sic) of NaCl, and that the yellowish-white powder dissolved readily in 8–10 ml. of sterile water.

Certain information concerning the chemistry and pharmaceutical formulation of cisplatin are given on pages 1–5 and 31–32 of the publication entitled "CLINICAL BROCHURE, CIS-PLATINUM (II) DIAMMINEDICHLORIDE (NSC-119875)", H. Handelsman et al., Investigational Drug Branch, Cancer Chemotherapy Evaluation Program, Division of Cancer Treatment, National Cancer Institute (Revised August 1974). Pages 31 and 32 thereof concern the formulation of cisplatin supplied gratis by the N.C.I. to clinicians for their clinical evaluation in the chemotherapy of cancer and read as follows:

| PHARMACEUTICAL DATA SHEET | |
|---|---|
| NSC-119875 | Cis-Diamminedichloroplatinum (II) |
| Dosage Formulation | |
| 10 mg./vial | The contents of each 20 ml. flint vial appears as an off-white lyophilized cake. Each vial contains 10 mg. of NSC-119875; 90 mg. of Sodium Chloride; 100 mg. of Mannitol and Hydrochloric acid for pH adjustment. |
| Solution Preparation | |
| 10 mg./vial | When reconstituted with 10 ml. of Sterile Water for Injection, USP, each ml. of the resulting solution will contain 1 mg. of NSC-119875, 10 mg. of Mannitol, and 9 mg. of Sodium Chloride having a pH range of 3.5–4.5. |
| Storage | The dry, unopened vials should be stored at refrigeration temperatures (4–8° C.). |
| Stability | Intact vials have a provisional stability of one year when stored at refrigeration temperature (4–8° C.). Stability recommendations may be adjusted pending completion of a two-year shelf-life study. Reconstitution as recommended results in a pale, yellow solution which is stable for not more than one hour at room temperature (22° C.) when exposed to normal room illumination and not more than eight hours at room temperature (22° C.) when protected from light. Reconstituted solutions may form a precipitate after one hour at refrigeration temperature |

-continued

| PHARMACEUTICAL DATA SHEET | |
|---|---|
| NSC-119875 | Cis-Diamminedichloroplatinum (II) |
| | (4–8° C.). |
| Caution | The lyophilized dosage formulations contain no preservatives and therefore it is advised to discard solutions eight hours after reconstitution. |

August, 1974
Clinical Drug Distribution Section
Drug Development Branch

Complete Disclosure

The present invention provides a stable, microcrystalline form of cisplatin which is rapidly soluble in water, and a process for its preparation. The present invention also provides a sterile, stable, dry-mix of said microcrystalline form of cisplatin suitable for rapid reconstitution with sterile water and intravenous administration to man; said dry-mix optionally containing a sterile, nontoxic, pharmaceutically acceptable, inorganic source of chloride ions in an amount equivalent to that produced by the presence of sodium chloride in a concentration of from about 1 to about 20 mgs., and preferably about 9 mgs., per mg. of microcrystalline cisplatin; said dry-mix also optionally containing a customary, harmless, physiologically acceptable excipient, which is preferably mannitol, in a concentration of from about 2 mgs. to about 150 mgs., and preferably about 10 mgs., per mg. of microcrystalline ciplatin; said dry-mix being completely soluble in sterile water within about three minutes (and usually within about two minutes), at a concentration of 1 mg. of microcrystalline cisplatin per ml. of sterile water.

There is also provided by the present invention a sterile, stable, dry-mix of microcrystalline cisplatin in a sealed container such as an ampul or vial, in unit dosage form, suitable for rapid reconstitution with sterile water and intravenous administration to man; said dry-mix formulation comprising, per ml. of sterile water to be used for reconstitution, from about 0.1 to about 1 mg., and preferably about 1 mg., of sterile microcrystalline cisplatin; said dry-mix optionally containing, per ml. of sterile water to be used for reconstitution, a sterile, nontoxic, pharmaceutically acceptable, inorganic source of chloride ions in an amount equivalent to that produced by the presence of from about 1 to about 20 mgs., and preferably about 9 mgs., of sodium chloride; said dry-mix also optionally containing, per ml. of sterile water to be used for reconstitution, from about 2 to about 150 mgs., and preferably about 10 mg., of a customary, harmless, physiologically acceptable excipient, which is preferably mannitol; said dry-mix being completely soluble in sterile water within about three minutes (and usually within about two minutes), at a concentration of 1 mg. of microcrystalline cisplatin per ml. of sterile water.

There is further provided by the present invention a process for the preparation of microcrystalline cisplatin which comprises the consecutive steps of (a) providing a first solution comprising a liquid organic amide, and preferably a tertiary amide, and most preferably dimethylformamide, containing, by volume, from about 1% to about 20%, and preferably about 10%, of aqueous hydrochloric acid having a concentration of about 6 N to about 12 N, and preferably about 12 N;

(b) dissolving cisplatin in said first solution in an amount of from about 10 to about 60 grams, and preferably about 40 grams, per liter of said first solution, to provide a second solution;

(c) admixing said second solution, with agitation, with from about 0.5 to about 5 volumes, and preferably from about 0.75 to about 2.5 volumes, and most preferably about 2 volumes, of water or dilute aqueous hydrochloric acid having a concentration up to about 0.2 N, and preferably about 0.1 N, at a temperature of from about 10° C. to about 40° C., and preferably at about room temperature, to form microcrystalline cisplatin;

(d) recovering the microcrystalline cisplatin by filtration;

(e) washing the recovered microcrystalline cisplatin with water or aqueous hydrochloric acid having a concentration up to about 0.2 N, and preferably about 0.1 N;

(f) optionally further washing the microcrystalline cisplatin with a non-reactive, water-miscible, volatile, organic solvent, preferably selected from (lower)alkanols and di(lower)alkyl ketones; and (g) optionally drying the washed microcrystalline cisplatin.

Practical considerations dictate that a medicament which requires reconstitution with water to form a solution before administration by a physician be rapidly soluble in the appropriate amount of water, so as to avoid time-wasting and tiresome periods of shaking by the physician or his assitant. Cisplatin, as prepared by the usual manufacturing procedures typically requires 10–25 minutes to dissolve in water at a concentration of 1 mg./ml., even if first screened to 200 mesh. The same period of time is required to dissolve cisplatin at the same concentration in an aqueous vehicle containing 9 mg./ml. of sodium chloride and 10 mg./ml. of mannitol, or to dissolve a mixture of cisplatin, sodium chloride and mannitol (in a weight ratio of 1:9:10) in water at a concentration of 1 mg. cisplatin per ml.

Cisplatin is commercially available at the present time for cancer chemotherapy under the trademark PLATINOL. It is supplied in unit dosage form in a vial as a lyophilized powder containing 10 mg. of cisplatin, 90 mg. of sodium chloride and 100 mg. of mannitol, and is to be reconstituted with 10 ml. of sterile water. Reconstitution of this product may be accomplished within three minutes of shaking. However, the manufacturing process requires lyophilization of the individual vials of an aqueous solution of cisplatin, sodium chloride, mannitol and dilute HCl, which is an expensive and time-consuming batch process. Thus, a commercial-sized lyophilized operation of, for example, 40,000 vials would require about 4–6 days for completion. This procedure includes loading the vials on the shelves of the chamber, freezing the solutions, evacuating the chamber until lyophilization is complete, adjusting the temperature of the chamber to above room temperature to complete the drying, admission of air into the chamber, sealing the vials and unloading the chamber. A typical sterile dry filling operation, on the other hand, utilizing a single filling machine to fill 200 mg. of solids per vial, may be expected to produce about 40,000 filled and sealed vials per 8-hour shift. In addition, because the solubility of cisplatin is only about 1 mg./ml., the cost of preparing dosage forms containing more than about 25 mg. of cisplatin per vial by lyophilization becomes prohibitive because of the large volume of water to be removed. Such dosage forms may, however, readily be prepared by sterile dry-filling techniques. Further disadvantages of lyophilization include the possibility of a power failure during the long cycle period, which would normally mean that the entire batch of cisplatin must be discarded. Also, HCl removed during lyophilization may corrode the lyophilizer chamber and system.

Both the N.C.I. Pharmaceutical Data Sheet for Cisplatin and the Official Package Circular for PLATINOL (cisplatin) discussed above state that the unopened vial of lyophilized product must be stored at refrigerator temperature. Stability tests on microcrystalline cisplatin and dry-mix formulations thereof indicate good stability at room temperature. Stability tests of 3 batches of microcrystalline cisplatin each showed less than a 1% loss after aging 3 months at 56° C. and 45° C., 4 months at 37° C. and 10 months at 25° C. when packed in amber colored glass vials sealed with teflon coated rubber stoppers and nested in cardboard cartons. Less than a 1.7% loss occurred with microcrystalline cisplatin packaged in amber glass vials and teflon coated rubber stoppers, when tested under accelerated light conditions at room temperature for one month without cartons.

Stability tests were also conducted on microcrystalline cisplatin dry-mix formulations containing 10 mg. of microcrystalline cisplatin, 90 mg. of sodium chloride and 100 mg. of mannitol packaged in amber colored glass vials sealed with teflon coated rubber stoppers. Potency losses observed after aging 2 and 3 months at 56° C. and 45° C. were less than 7%; losses after 4 and 6 months at 37° C. were less than 5%; and losses after 10 and 11 months at 25° C. were less than 6%.

Microcrystalline cisplatin provided by the present invention has a particle size distribution of at least about 80% in the 0-5 micrometer range and less than about 20% in the 5-20 micrometer range, with essentially no particles greater than 20 micrometers. When prepared under preferred conditions the microcrystalline cisplatin typically contains no particles greater than 10 micrometers. This particle size distribution is of the same order as cisplatin which has been lyophilized from dilute hydrochloric acid and is significantly smaller than the typical particle size of machine micronized pharmaceuticals. Table 1, below, shows the microscopic particle size evaluation of three batches of microcrystalline cisplatin, one batch of lyophilized cisplatin (from 0.07 N HCl) and a typical batch of commercial machine micronized benzathine cephapirin.

TABLE 1

| Material | Particle Size Distribution (%) Micrometers | | | |
|---|---|---|---|---|
| | 0-5 | 5-10 | 10-20 | 10-730 |
| Microcrystalline cisplatin (No. 759) | 96 | 4 | 0 | — |
| Microcrystalline cisplatin (No. 315) | 82 | 14 | 4 | — |
| Microcrystalline cisplatin (No. 277) | 85 | 15 | 0 | — |
| Lyophilized cisplatin (No. 276) | 97 | 3 | 0 | — |
| Machine micronized benzathine cephapirin (No. 158) | 11.3 | 85.5 | — | 3.4 |

Although particle size distribution studies indicate that the particle size of microcrystalline cisplatin is of the same order as that of lyophilized cisplatin, and simple microscopic examination shows that microcrystalline cisplatin differs markedly in particle size from regular (bulk) cisplatin, the situation is reversed in terms of crystal structure. X-ray powder diffraction patterns show that microcrystalline cisplatin and lyophilized cisplatin are clearly different crystalline forms, and that microcrystllline cisplatin and regular cisplatin are of the same crystalline form (minor differences in the diffraction patterns being due to differene in particle size, packing in the capillary, etc.). Table 2 gives the data obtained from X-ray powder diffraction studies (filtered Cu Kα radiation, 1.54051 angstroms) of regular cisplatin, microcrystalline cisplatin and lyophilized cisplatin.

TABLE 2

X-ray Data For Different Forms Of Cisplatin

| Sample | Two Theta (Degrees) | Relative Intensity | Interplanar Spacings (Angstroms) |
|---|---|---|---|
| Regular Cisplatin (No. 389) | 13.89 | 100 | 6.370 |
| | 15.00 | 49 | 5.901 |
| | 16.30 | 28 | 5.433 |
| | 24.10 | 11 | 3.690 |
| | 26.84 | 40 | 3.319 |
| | 28.37 | 18 | 3.143 |
| | 38.30 | 3 | 2.348 |
| Lyophilized Cisplatin (No. 359) | 12.51 | 5 | 7.070 |
| | 12.76 | 5 | 6.932 |
| | 13.88 | 100 | 6.375 |
| | 14.13 | 100 | 6.263 |
| | 19.90 | 6 | 4.458 |
| | 20.19 | 66 | 4.394 |
| | 28.11 | 8 | 3.172 |
| | 28.71 | 9 | 3.107 |
| | 31.90 | 4 | 2.803 |
| Microcrystalline Cisplatin (No. 705) | 13.81 | 100 | 6.407 |
| | 14.93 | 84 | 5.929 |
| | 16.26 | 71 | 5.447 |
| | 24.05 | 27 | 3.697 |
| | 26.57 | 22 | 3.352 |
| | 28.37 | 16 | 3.143 |
| | 30.35 | 13 | 2.943 |
| | 33.14 | 15 | 2.701 |

In preparing the microcrystalline cisplatin of the present invention, regular (bulk) cisplatin is first dissolved in a solution of a liquid organic amide and hydrochloric acid. Suitable amides will be apparent to those skilled in the art, the requirements being stability of the amide and sufficient solubility of cisplatin in the amide-HCl mixture. Amides suitable for use in this process include, for example, formamide, N-methylformamide, N,N-dimethylformamide, N-ethylformamide, N,N-diethylformamide, N,N-diethylacetamide, N,N-diethylacetamide, N-(2-hydroxyethyl)acetamide, N-methyl-2-pyrrolidinone, and the like. We prefer to utilize tertiary amides such as the N,N-dialkylformamides and N,N-dialkylacetamides. The most preferred amide is N,N-dimethylformamide. It is preferred that high quality amide be utilized in this process. In parallel experiments utilizing (a) reagent quality DMF and (b) low quality technical grade DMF, we found that the lower quality DMF decreased the yield of product by about 4% and increased the solubility time of the product to about five minutes.

The composition of the amide-HCl solution may vary from about 1% (volume) to about 20% (volume) of hydrochloric acid, and the concentration of the hydrochloric acid may vary from about 6 N to about 12 N. The optimum composition of the amide-HCl solution for any given amide can be readily determined by those skilled in the art by routine testing. With the preferred amide, N,N-dimethylformamide, we prefer to utilize an amide-HCl solution comprising about 90% (volume)

amide and about 10% (volume) of about 12 N HCl. It should be noted that too high a concentration of HCl may cause some degradation of the cisplatin.

Depending on the particular amide utilized and the composition of the amide—HCl solution, from about 10 to about 60 grams of cisplatin may be dissolved per liter of amide—HCl solution. With many amide—HCl solutions significantly more than 60 grams of cisplatin may physically be dissolver per liter, but we have found that subsequent crystallization from too highly concentrated solutions gives a product which will not completely dissolve in 3 minutes. At the lower end, we have found that less than about 10 grams of cisplatin per liter usually gives significantly decreased yields and, of course, requires inordinately high volumes of solution for a given amount of product. Using the preferred DMF-concentrated HCl solution (about 9:1 by volume), we prefer to utilize about 40 grams of cisplatin per liter.

The crystallization step may be conducted at a temperature of from about 10° C. to about 35° C. At the higher temperatures the yield of product is lower due to increased solubility. At temperatures below about 10° C. we have found that the product often has solubility times in excess of 3 minutes. It is believed that this is due to the product being too quickly "shocked" out of solution rather than somewhat more slowly growing the proper microcrystalline cisplatin. But this is only a theoretical concept and does not form part of the invention. It is, of course, most convenient to conduct the crystallization step at room temperature and, since excellent yields of high quality microcrystalline cisplatin are obtained at room temperature, (e.g. 20°-25° C.), this is our preferred crystallization temperature.

Crystallization is effected by admixing the amide-HCl solution of cisplatin with from about 0.5 to about 5 volumes of water or dilute HCl having a concentration up to about 0.2 N. The cisplatin solution may be added to the water (or dilute aqueous HCl), or the converse. Each procedure gives substantially the same yield and quality of microcrystalline cisplatin. The optimum volume of water (or dilute aqueous HCl) to be admixed with the cisplatin solution depends on the particular amide utilized as well as the composition of the amide-HCl-cisplatin solution. The optimum volume for any given cisplatin solution may be determined by routine testing. Generally, we prefer to utilize about 1.5 to about 2.5 volumes of water (or dilute aqueous HCl) per volume of amide-HCl-cisplatin solution. When using the preferred DMF-concentrated HCl (9:1 by volume) containing about 40 grams of cisplatin per liter, we prefer to use about 2 volumes of water (or dilute aqueous HCl) per volume of DMF-HCl-cisplatin solution. It should be noted that the use of too great a volume of water (or dilute aqueous HCl) tends to also crystallize out impurities which were in the starting cisplatin, e.g., transplatinum.

As pointed out above, microcrystalline cisplatin may be crystallized from its amide-HCl solution by the addition of water or dilute aqueous HCl. The choice between the two is not critical, and we prefer to be guided by the amount and concentration of HCl present in the amide-HCl-cisplatin solution. Thus, if that solution contained a relatively low amount of HCl, near the lower limit of about 1% of 6 N HCl, we would prefer to use approximately 0.2 N HCl to effect the crystallization. Conversely if the amide-HCl-cisplatin solution contained a large amount of HCl, near the upper limit of 20% of 12 N HCl, we would prefer to utilize water to effect the crystallization. When using our preferred DMF-concentrated HCl (9:1) containing about 40 grams of cisplatin per liter, we prefer to utilize approximately 0.1 N HCl to effect the crystallization.

The microcrystalline cisplatin provided by the present invention (after sterilization) may be packaged alone in a sealed container such an an ampul or vial, preferably in unit dosage form, for reconstitution with sterile water (at least 1 ml. per mg. of microcrystalline cisplatin) to produce a solution suitable for intravenous administration. Alternatively, the microcrystalline cisplatin may be admixed with a sterile, nontoxic, pharmaceutically acceptable, inorganic source of chloride ions in an amount equivalent to that produced by the presence of sodium chloride in a concentration of from about 1 to about 20 mgs. (and preferably about 9 mgs.) per mg. of microcrystalline cisplatin. Preferably, the source of chloride ions is sodium chloride. In another embodiment, the sterile microcrystalline cisplatin may be admixed with a sterile, customary, harmless, physiologically acceptable excipient, which is preferably mannitol, in an amount of from about 2 mg. to about 150 mg. (and preferably about 10 mg.) per mg. of sterile microcrystalline cisplatin. In still another embodiment, the sterile microcrystalline cisplatin may be admixed with both the aforementioned source of chloride ion and excipient in the amounts mentioned. Each of these dry-mixes is then packaged in a sealed container such as an ampul or vial, preferably in unit dosage form, for reconstitution with sterile water (at least 1 ml. per mg. of microcrystalline cisplatin) to produce a solution suitable for intravenous administration. The aforementioned dry-mixes may be prepared by simple dry blending of the desired ingredients or by wet granulation techniques, both of which are well known in the art. With wet granulation procedures, it is preferred that a granulation be made of all ingredients except the cisplatin and that, after drying, the granulation be admixed with the desired amount of microcrystalline cisplatin.

The microcrystalline cisplatin of the present invention, and dry-mixes thereof, are readily soluble in sterile water (at least 1 ml. per ml. of microcrystalline cisplatin) within about three minutes. The reconstituted solution, if not used immediately, should be stored at about room temperature. Refrigeration at temperatures below about 10° C. results in crystallization of cisplatin which is not in the microcrystalline form. This cisplatin is exceedingly difficult to redissolve at room temperature, but solution can be obtained by heating to about 35°-40° C.

Cisplatin is an inorganic compound first noted to prevent replication of E. coli and subsequently found to possess antitumor activity. The drug exerts its effect of interfering with DNA synthesis by causing cross-linking of complementary strands of DNA. It has activity in a variety of tumor systems including L1210, Sarcoma 180, Walker 256 carcinosarcoma, DMBA induced mammary tumors and ascitic B16 melanosarcoma. The compound is especially interesting in that it exhibits synergism with a large number of currently-used chemotherapeutic agents. Large animal toxicology studies showed renal tubular necrosis, enterocolitis, bone marrow hypoplasia and lymphoid atrophy. Phase I studies have demonstrated the following toxicities: myelosuppression, renal insufficiency, high frequency ototoxicity and GI intolerance. Currently used dosages with mild to moderately acceptable toxicity are in the range of 60–100 mg./m$^2$ IV as a single dose or divided over 3–5 days, to be repeated at four-week intervals. Early clinical trials show some responses to the drug in germinal cell tumors, lymphomas, sarcomas, breast and head and neck carcinomas.

A dosage of 60 mg./m² is roughly equal to 1.5 mg./kg. which in turn is roughly equal to 105 mg./patient weighing 70 kg.

The microcrystalline cisplatin of the present invention, or dry-mixes thereof, after reconstitution, are used in the same manner and for the same purpose as stated above and in the other publications and in the voluminous medical literature on this subject. As stated therein, frequent use is made of concurrent therapy with other chemotherapeutic agents for best results. When desired, the solutions of the present invention may be added immediately before use to a sterile, pharmaceutically acceptable aqueous diluent such as glucose or saline. Administration is either by direct intravenous injection or by intravenous infusion.

"Platinol" is a registered trademark of Bristol-Myers Company for cisplatin.

"Darco" is a registered trademark of Atlas Chemical Industries for activated carbon.

"Millipore" is a registered trademark of the Millipore Corporation for membrane filters.

EXAMPLE 1

Preparation of Microcrystalline Cisplatin

To a solution of 0.7 ml. of 1 N HCl and 6.3 ml. of dimethylformamide (DMF) was added 280 mg. of cisplatin, and the mixture was stirred for 1 hour without obtaining a complete solution. An additional 2 ml. of DMF and 0.7 ml. of concentrated HCl were added, and the resulting solution was stirred for 1 hour and then divided into two parts.

(a) To one part of the above solution (4.9 ml.) was added 20 ml. of 0.1 N HCl, and the resulting precipitate was slurried for 15 minutes. The solids were recovered by filtration, washed with 1.5 ml. of 0.1 N HCl and 3 ml. of acetone, and dried in vacuo at 20° C. for 18 hours. The yield of microcrystalline cisplatin was 93 mg. (66%). Karl Fischer analysis showed the product to be free of water and NMR analysis showed it to be free of DMF and acetone.

Anal. Calc'd for $PtH_6N_2Cl_2$: H, 2.02; N, 9.34; Cl, 23.63; Found: H, 1.89; N, 9.33; Cl, 22.59.

Ten mg. of the above microcrystalline cisplatin was weighed into a 17 ml. vial along with 90 mg. of NaCl and 100 mg. of mannitol. To this mixture was added 9.9 ml. of sterile water, and complete solution was obtained within 1 minute of shaking. Another 10 mg. portion of the above microcrystalline cisplatin was shaken with 10 ml. of an aqueous solution of NaCl (90 mg./10 ml.) and mannitol (100 mg./10 ml.) and dissolved completely within 1 minute.

(b) The other part of the above solution (4.8 ml.) was added to 20 ml. of 0.1 N HCl and the resulting precipitate was slurried for 15 minutes. The solids were recovered by filtration, washed with 1.5 ml. of 0.1 N HCl and 3 ml. of acetone, and dried in vacuo at 20° C. for 18 hours. The yield of microcrystalline cisplatin was 98 mg. (70%). A 10 mg. portion of this product was shaken with 10 ml. of an aqueous solution of NaCl (90 mg./10 ml.) and mannitol (100 mg./10 ml.) and dissolved completely within 1 minute.

EXAMPLE 2

Preparation Of Microcrystalline Cisplatin

Cisplatin (280 mg.) was dissolved in 7.0 ml. of a DMF-HCl solution prepared by mixing 0.7 ml. of concentrated HCl and 6.3 ml. of DMF. The solution was stirred for 1 hour and then 14 ml. of 0.1 N HCl was added. The resulting precipitate was slurried for 15 minutes and the solids were then recovered by filtration, washed with 2 ml. of 0° C. 0.1 N HCl and 4 ml. of acetone, and dried in vacuo at 20° C. for 20 hours. The yield of microcrystalline cisplatin was 225 mg. (80%). A 10 mg. sample of this product was shaken with 10 ml. of an aqueous solution of NaCl (90 mg./10 ml.) and mannitol (100 mg./10 ml.) and dissolved completely within 3 minutes. Another 10 mg. sample of the product was mixed with 90 mg. of NaCl and 100 mg. of mannitol, and this dry-mix formulation was completely soluble in 9.9 ml. of water within 3 minutes.

EXAMPLE 3

Preparation Of Microcrystalline Cisplatin

Cisplatin (210 mg.) was added to 3 ml. of a DMF-HCl solution prepared by mixing 0.3 ml. of concentrated HCl and 2.7 ml. of DMF. Complete solution was not obtained after 1 hour of stirring so an additional 0.1 ml. of concentrated HCl and 0.9 ml. of DMF was added. The resulting solution was stirred for 1 hour and 8 ml. of 0.1 N HCl was then added. The resulting precipitate was slurried for 15 minutes and the solids were then recovered by filtration, washed with 1.5 ml. of 0.1 N HCl and 2 ml. of acetone, and dried in vacuo at 20° C. for 20 hours. The yield of microcrystalline cisplatin was 162 mg. (77%).

EXAMPLE 4

Preparation Of Microcrystalline Cisplatin

Cisplatin (210 mg.) was dissolved in 5.25 ml. of a solution of DMF-HCl (9:1). The solution was stirred for 1 hour and 10.5 ml. of 0.1 N HCl was then added. The resulting precipitate was slurried for 15 minutes and the solids were then recovered by filtration, washed with 1 ml. of 0.1 N HCl and 2 ml. of acetone, and dried in vacuo at 20° C. for 18 hours. The yield of microcrystalline cisplatin was 168 mg. (80%). Ten mg. of this product was shaken with 10 ml. of an aqueous solution of NaCl (90 mg./10 ml.) and mannitol (100 mg./10 ml.) and dissolved completely within 2 minutes. An additional 10 mg. of this product was mixed with 90 mg. of NaCl and 100 mg. of mannitol and the dry-mix was completely soluble in 9.9 ml. of sterile water within 2 minutes of shaking.

EXAMPLE 5

Preparation Of Microcrystalline Cisplatin

Cisplatin (1.0 g) was dissolved in 25 ml. of DMF-HCl (9:1) solution. The clear solution was stirred for 1 hour under a nitrogen atmosphere and 50 ml. of 0.1 N HCl was then added. The resulting precipitate was slurried for 15 minutes and the solids were then recovered by filtration and washed with 5 ml. of 4° C. 0.1 N HCl and 10 ml. of acetone. About one-fourth of the solids were dried in vacuo at 40° C. for 18 hours to give 0.120 g of product. The remainder of the solids were dried in vacuo at 20° C. for 18 hours to give 0.682 g of product.

Total yield of microcrystalline cisplatin was 0.802 g (80%).

A ten mg. sample of each of the dried products was shaken with 10 ml. of an aqueous solution containing NaCl (90 mg./10 ml.) and mannitol (100 mg./10 ml.), and each was found to be completely soluble within 3 minutes.

Thin layer chromatography (TLC) of the two products did not detect any impurities in either. High performance liquid chromatography (HPLC) of the two products indicated a potency of 984 mcg./mg. for the material dried at 40° C. and a potency of 1027 mcg./mg. for the material dried at 20° C.

Anal. Calc'd for $PtH_6N_2Cl_2$: H, 2.02; N, 9.34; Cl, 23.63; (Dried at 40° C.) Found: H, 1.77; N, 9.31; Cl, 23.29; (Dried at 20° C.) Found: H, 1.79; N, 9.21; Cl, 23.13.

EXAMPLE 6

Preparation Of Microcrystalline Cisplatin

Cisplatin (2.5 g) was dissolved in 62.5 ml. of DMF-HCl solution (prepared by dissolving 15 ml. concentrated HCl in 135 ml. of DMF). The solution was stirred for 1 hour under nitrogen and 125 ml. of 0.1 N HCl was then added. The resulting precipitate was slurried for 15 minutes and the solids were then recovered by filtration, washed with 12 ml. of 0.1 N HCl and 25 ml. of acetone, and dried in vacuo at 20° C. for 18 hours. The yield of microcrystalline cisplatin was 2.0 g (80%). A 10 mg. sample of the product was shaken with 10 ml. of an aqueous solution containing NaCl (90 mg./10 ml.) and mannitol (100 mg./10 ml.), and was completely soluble within 2 minutes.

A dry-mix formulation was prepared by thoroughly mixing 750 mg. of the above product (200 mesh), 6.75 g of NaCl (200 mesh) and 7.5 g of mannitol (200 mesh).

EXAMPLE 7

Purification Of Sodium Chloride

NaCl (18.5 g) was dissolved in 62 ml. of distilled water. To this solution was added 1.85 g of activated carbon (Darco KB), and the mixture was stirred for 0.5 hour. The carbon was removed by filtration through hard filter paper and the filtrate was slowly added to 62 ml. of rapidly stirred concentrated HCl. The resulting precipitate was slurried for 0.5 hour, recovered by filtration through hard filter paper and dried at 100° C. for 18 hours. The yield of product was 13.8 g (75%).

EXAMPLE 8

Purification Of Mannitol

Mannitol (10 g) was dissolved in 67 ml. of distilled water. Activated carbon (1.0 g, Darco KB) was added and the mixture was stirred for 0.5 hour. The mixture was then filtered through hard filter paper and the filtrate was slowly added to 335 ml. of rapidly stirred acetone. The resulting precipitate was slurried for 0.5 hour, recovered by filtration through hard filter paper and dried at 100° C. for 18 hours. The yield of product was 8.0 g (80%).

EXAMPLE 9

Preparation Of Sterile Dry-Fill Cisplatin For Injection (10 Mg. Cisplatin Per Vial)

A. Preparation Of Sterile Microcrystalline Cisplatin

Precautions

All personnel involved with handling of this product should protect themselves as follows:
(a) Wear face mask, eye protection, gloves and protective clothing during manufacturing, processing and packaging.
(b) Avoid any and all contact with the drug by inhalation or dermal contact.
(c) Clean all equipment and the manufacturing area thoroughly to remove a possible drug contamination.

Procedure

1. Place 90 ml. of dimethylformamide* into a suitable glass container and maintain an overlay of nitrogen. Start and maintain rapid stirring. Slowly add 10 ml. of concentrated hydrochloric acid, U.S.P.. Maintain the temperature in the range of 20° to 27° C.

*The dimethylformamide should be free of dimethylamine and approximately equivalent in purity to Burdick and Jackson Laboratories, Dimethylformamide, Distilled In Glass or Fisher Certified (ACS) Dimethylformamide, List D-119.

2. Continue to rapidly stir the 100 ml. of freshly prepared solution under a blanket of nitrogen maintaining the temperature in the range of 20°-27° C.

3. Slowly add 4 grams of cisplatin over a 5-minute interval. Continue rapid stirring under a blanket of nitrogen for 1 hour. A solution or near solution is obtained.

4. Using nitrogen pressure pass the solution through a sterile 0.22 micrometer Millipore filter into a suitable sterile, pyrogen-free glass container using aseptic technique in a sterile area.

5. To the filtrate maintained under rapid stirring, add, over a 5-minute interval, 200 ml. of 20°-27° C. sterile, pyrogen-free 0.1 N hydrochloric acid. Dense, yellow microcrystals form. Stir for 15 minutes.

6. Using aseptic technique, isolate the crystals by suitable filtration. Suck the filter cake to an apparent dryness. Do not pass excess air through the filter cake. Retain the filtrate.

7. Wash the filter cake with 10 ml. of 20°-27° C., sterile, pyrogen-free 0.1 N hydrochloric acid. Add the wash to the Step 6 filtrate. Suck the filter cake to an apparent dryness. Do not pass excess air through the filter cake.

Wash the filter cake with 20 ml. of sterile, pyrogen-free acetone. Add the wash to the filtrate. Suck the filter cake to an apparent dryness. Do not pass excess air through the filter cake. (Save the combined filtrates. Recovery of cisplatin from the filtrate is described in Step 9 which follows.)

8. Using aseptic technique, remove and high-vacuum dry the microcrystalline cisplatin (in the absence of light) for 24 hours at 37°-42° C. Yield: Approximately 3.3-3.5 grams (80-86% yield). Store the yellow microcrystals in a suitable, sterile, pyrogen-free amber glass container capped with a metal screw cap containing a teflon or polyethylene liner at controlled Room Temperature in the absence of light.

9.
(a) Cool the filtrate of Step 7 above with stirring to 0°-4° C. Aseptic conditions are not required. Hold the mixture without stirring for 48 hours at 0°–4° C. Golden crystals are deposited. Remove the crystals by filtration. Wash with 20 ml. of acetone and high-vacuum dry the crystals (in the absence of light) at 37°–42° C. for 24 hours. Yield: Approximately 0.2 g. (5% yield). These crystals do not have the solution properties of the microcrystalline form and should be reworked via the above procedure to yield microcrystalline cisplatin.

(b) The platinum compounds remaining in the filtrate may be recovered by distillation of the water and dimethylformamide.

Properties Of Sterile Microcrystalline Cisplatin As Prepared By Above Procedure

1. H.P.L.C. Assay: Single peak of 2.8 minutes retention time (1028 mcg./mg.).
2. IR: Consistent for structure.
3. NMR: In T.F.A.; no evidence of acetone or dimethylformamide.
4. Elemental Analysis: Consistent for formula; product appears anhydrous.
5. Crystal Morphology: At 250X in mineral oil using the polarizing microscope, the microcrystals appear as very small rods showing specific extinction. The parent cisplatin appears as very large irregular plates (possibly hundreds of times the size of the microcrystals) showing a birefringence of the color spectrum.

B. Preparation Of Sterile Sodium Chloride

1. Place 90 ml. of Sterile Water for Injection, U.S.P. into a suitable glass container. Start stirring and maintain the temperature in the range of 20°–26° C. Add and dissolve 27 grams of sodium chloride. Maintain stirring until solution is obtained.
2. Continue stirring and add 2.7 grams of Darco KB activated carbon. Maintain stirring for 1.0 hour.
3. Remove the carbon by filtration. Wash the carbon cake with 5 ml. of Sterile Water for Injection. Add the wash to the filtrate.
4. Using nitrogen pressure and aseptic technique, pass the filtrate through a suitable, sterile, pyrogen-free 0.22 micrometer Millipore filter into a suitable, sterile, pyrogen-free glass container. This is Solution A.
5. Using aseptic technique, add 5 volumes (approximately 550 ml.) of acetone which has been filtered through a sterile 0.22 micrometer Millipore filter to the rapidly stirring Millipore filtered Solution A over a 10 minute interval. (Alternatively, Solution A may be added to 550 ml. of rapidly stirring acetone which has been filtered through a sterile 0.22 micrometer Millipore filter.) Crystals form.
6. Maintain stirring at room temperature for 0.5 hour.
7. Remove the crystals by suitable filtration using aseptic technique.
8. Wash the crystals on the filter with two 40 ml. portions of acetone which has been filtered through a sterile 0.22 micron Millipore filter.
9. Using aseptic technique, remove the crystals from the filter and air-dry at 115°–125° C. for 24 hours. Yield: Approximately 21.5 grams (80% yield).
10. Store the crystals in a suitable, sterile, pyrogenfree amber glass container capped with a metal screw cap containing a teflon or polyethylene liner.

Properties Of Sterile Sodium Chloride Prepared By Above Procedure

1. Acetone not detectable by NMR.
2. Water (Karl Fisher)=Typically about 1%

C. Preparation Of Sterile Mannitol

1. Place 90 ml. of Sterile Water for Injection, U.S.P. into a suitable glass container. Start stirring and maintain the temperature in the range of 20°–26° C. Add and dissolve 13.6 grams of mannitol. Maintain stirring until solution is obtained.
2. Continue stirring and add 1.4 grams of Darco KB activated carbon. Maintain stirring for 1 hour.
3. Remove the carbon by filtration. Wash the carbon cake with 5 ml. of Sterile Water for Injection, U.S.P. Add the wash to the filtrate.
4. Using nitrogen pressure and aseptic technique, pass the filtrate through a suitable, sterile, pyrogen-free 0.22 micrometer Millipore filter into a suitable sterile, pyrogen-free glass container.
5. Using aseptic technique, add to the filtrate, with rapid stirring and over a 10 minute interval, 500 ml. of acetone which has been filtered through a sterile 0.22 micrometer Millipore filter. Crystals form. (Alternatively, the filtrate may be added over a 10 minute interval to 500 ml. of rapidly stirring acetone which has been filtered through a sterile 0.22 micrometer Millipore filter.) Maintain stirring for 0.5 hour at room temperature.
6. Remove the crystals by suitable filtration using aseptic technique.
7. Wash the crystals on the filter with two 20 ml. portions of acetone which has been filtered through a sterile 0.22 micrometer Millipore filter.
8. Using aseptic technique remove the crystals from the filter and air-dry at 100°–115° C. for 24 hours. Yield: Approximately 11.4 grams (84% yield).
9. Store the crystals in a suitable, sterile, pyrogenfree amber glass container capped with a metal screw cap containing a teflon liner.

Properties Of Sterile Mannitol Prepared By Above Procedure

1. No acetone detected by NMR.
2. Water (Karl Fisher)=Typically about 0.4–1%

D. Preparation Of A Sterile Granulation Of Mannitol And Sodium Chloride For Use In Sterile Dry-Fill Microcrystalline Cisplatin For Injection

| Formula | | |
|---|---|---|
| | Per 10 mg. Cisplatin Vial | Per Ten Thousand 10 mg. Cisplatin Vial |
| Sterile Mannitol | 0.1000 Gram | 1000.00 Grams |
| Sterile Sodium Chloride | 0.0900 Gram | 900.00 Grams |
| Sterile Water For Injection, U.S.P. | 0.025 ml.* | 250.00 ml.* |

*The amount of water used may vary as a function of obtaining a wet granulation having suitable consistency. The water is removed during processing.

Manufacturing Instructions (Observe Safety Precautions Listed Below)

1. Using aseptic technique and appropriate sterile pyrogen-free equipment, separately mill the sterile, pyrogen-free mannitol and the sterile, pyrogen-free sodium chloride through a 40 mesh screen.
2. Using aseptic technique, place the required amounts of milled sterile, pyrogen-free mannitol and sodium chloride into an appropriate sterile, pyrogenfree blender. A jacketed vacuum V-Blender or Cone Blender equipped with an agitator bar is desirable. Blend for one hour.

3. In small increments add a sufficient amount of sterile, pyrogen-free Water for Injection, U.S.P.* through the agitator bar with the blender rotating until a granulation of suitable consistency is formed. After each addition of water for injection, run the agitator bar for two 5-minute periods during a one-half hour blending period.

*NOTE: The amount of water shown in the formula was determined in a small scale laboratory run. Depending on the equipment used for producing larger batches, the amount of water required to prepare a granulation with suitable consistency may vary from the indicated amount.

4. When a suitable granulation is obtained continue the blender rotation with agitator bar turned off and vacuumdry in the blender with the heating water in the jacket set at 50°–70° C. for 24 hours or until the water content is below 0.3%.

Alternatively, the blend may be removed from the blender and dried at 50° C.–60° C. in a sterile Devine vacuumoven for 48 hours.

5. Using aseptic technique pass the dried blend through a suitable sterile, pyrogen-free mill equipped with a sterile, pyrogen-free 60 mesh or equivalent screen.

6. Place the milled, sterile granulation into a suitable sterile, pyrogen-free blender and blend for a half hour or until content uniformity is obtained. The powder may be assayed for chloride content over time as a check for content uniformity.

7. Store the powder in suitable sterile, pyrogen-free amber glass containers capped with a metal screw cap containing a teflon or polyethylene liner. Alternately, the required amount of sterile blend may be left in the blender and the required amount of microcrystalline cisplatin added to produce Cisplatin for Injection.

Safety Precautions

All personnel involved with handling of this product should protect themselves as follows:

(a) Wear face mask, eye protection, gloves and protective clothing during manufacturing, processing and packaging.

(b) Avoid any and all contact with the drug by inhalation or dermal contact.

(c) Clean all equipment and the manufacturing area thoroughly to remove a possible drug contamination.

E. Sterile Dry-Fill Cisplatin For Injection (10 Mg. Cisplatin Per Vial

[Label Claim is 10 Mg. of Cis-Diamminedichloro Platinum II (Cisplatin) Per Vial]

Precautions

All personnel involved with batching of this product should adequately protect themselves as follows:

(a) Wear face mask, eye protection, gloves and protective clothing during manufacturing, processing and packaging.

(b) Avoid any and all inhalation of the drug or dermal contact.

(c) Clean all equipment and the manufacturing area thoroughly to remove possible future contamination.

Formula

| Ingredient | Per Vial | Per 100 Vials |
| --- | --- | --- |
| Sterile, Pyrogen-Free Microcrystalline Cisplatin | *0.0100 g. | 1.00 g. |
| Sterile, Pyrogen-Free Sodium Chloride (40 mesh) | 0.0900 g. | 9.00 g. |
| Sterile, Pyrogen-Free Mannitol (40 mesh) | 0.1000 g. | 10.00 g. |
| | 0.2000 g. | 20.00 g. |

*This weight of cisplatin assumes a potency of 1000 mcg./mg. To calculate the amount of cisplatin to use, apply the following formula:

$$\frac{1000 \times 0.0100 \text{ g.}}{\text{Potency of cisplatin in mcg./mg.}} = \text{Grams of cisplatin per vial}$$

Manufacturing Instructions

1. Using aseptic technique and appropriate sterile pyrogen-free equipment, separately mill the sterile, pyrogen-free mannitol and the sterile, pyrogen-free sodium chloride through a 40 mesh screen.

2. Mix the required amounts of screened, sterile, pyrogen-free sodium chloride and mannitol in appropriate sterile, pyrogen-free mixing or blending equipment for 1 hour. A V-Blender or Cone Blender equipped with an agitator bar is desirable.

3. Pass the microcrystalline cisplatin through a sterile 40 mesh screen to eliminate any lumps. To the blender containing the mixture from the preceding step (or the granulation from Step D, above) add the required amount of sterile, pyrogen-free microcrystalline cisplatin in three, separate and about equal increments. Blend for 30 minutes after each addition. Pass the mixture through a sterile 40 mesh screen and return to the blender. Mix for 30 minutes or longer until a uniform mixture is realized.

4. Drop the blend into suitable, sterile, pyrogen-free amber glass containers capped with a metal screw cap containing a teflon liner. Store the bulk in the dark.

5. Fill the required amount of mixture into suitable, sterile, pyrogen-free amber glass vials. Cap and seal with suitable, sterile, pyrogen-free teflon coated rubber stopper and seal with aluminum caps. Store the vials in the dark.

6. The 10 mg. cisplatin vial must be reconstituted with not less than 10 ml. of Sterile Water for Injection, U.S.P. at 22°–30° C. A clear solution should be obtained within 3 minutes of shaking. A pH of 4.0 to 5.5 is noted. Cisplatin solutions at a concentration greater than 0.5 mg./ml. should not be refrigerated since the cisplatin will crystalize out of solution.

We claim:

1. Stable, microcrystalline cisplatin having a particle size distribution of at least about 80% in the range of 0 to 5 micrometers, less than about 20% in the range of 5 to 20 micrometers and essentially no particles larger than 20 micrometers; the crystalline form of said microcrystalline cisplatin being different from that of lyophilized cisplatin as demonstrable by x-ray powder diffraction patterns; and said microcrystalline cisplatin being completely soluble in water within about three minutes at a concentration of 1 mg. per ml.

2. The microcrystalline cisplatin of claim 1 having an x-ray powder diffraction pattern substantially as follows:

| Two Theta (Degrees) | Relative Intensity | Interplanar Spacings (Angstroms) |
| --- | --- | --- |
| 13.81 | 100 | 6.407 |
| 14.93 | 84 | 5.929 |

-continued

| Two Theta (Degrees) | Relative Intensity | Interplanar Spacings (Angstroms) |
|---|---|---|
| 16.26 | 71 | 5.447 |
| 24.05 | 27 | 3.697 |
| 26.57 | 22 | 3.352 |
| 28.37 | 16 | 3.143 |
| 30.35 | 13 | 2.943 |
| 33.14 | 15 | 2.701 |

3. The microcrystalline cisplatin of claim 1 or 2 wherein said microcrystalline cisplatin is sterile.

4. Sterile, stable, microcrystalline cisplatin in a sealed container in unit dosage form, reconstitutable with sterile water within about three minutes at a concentration of 1 mg. of microcrystalline cisplatin per ml. of sterile water, and suitable for intravenous administration to man; said microcrystalline cisplatin having a particle size distribution of at least about 80% in the range of 0 to 5 micrometers, less than about 20% in the range of 5 to 20 micrometers and essentially no particles larger than 20 micrometers; the crystalline form of said microcrystalline cisplatin being different from that of lyophilized cisplatin as demonstrable by x-ray powder diffraction patterns.

5. The sterile unit dosage form of microcrystalline cisplatin of claim 4 wherein said microcrystalline cisplatin has an x-ray powder diffraction pattern substantially as follows:

| Two Theta (Degrees) | Relative Intensity | Interplanar Spacings (Angstroms) |
|---|---|---|
| 13.81 | 100 | 6.407 |
| 14.93 | 84 | 5.929 |
| 16.26 | 71 | 5.447 |
| 24.05 | 27 | 3.697 |
| 26.57 | 22 | 3.352 |
| 28.37 | 16 | 3.143 |
| 30.35 | 13 | 2.943 |
| 33.14 | 15 | 2.701 |

6. A sterile, stable, dry-mix of microcrystalline cisplatin in a sealed container in unit dosage form, reconstitutable with sterile water within about three minutes at a concentration of 1 mg. of microcrystalline cisplatin per ml. of sterile water, and suitable for intravenous administration to man; said dry-mix also containing a sterile, nontoxic, pharmaceutically acceptable, inorganic source of chloride ions in an amount equivalent to that produced by the presence of sodium chloride in a concentration of from about 1 to about 20 mgs. per mg. of microcrystalline cisplatin; said microcrystalline cisplatin having a particle size distribution of at least about 80% in the range of 0 to 5 micrometers, less than about 20% in the range of 5 to 20 micrometers and essentially no particles larger than 20 micrometers; the crystalline form of said microcrystalline cisplatin being different from that of lyophilized cisplatin as demonstrable by x-ray powder diffraction patterns.

7. The dry-mix of claim 6 wherein the inorganic source of chloride ions is sodium chloride.

8. The dry-mix of claim 7 wherein the sodium chloride is present at a concentration of about 9 mg. per mg. of microcrystalline cisplatin.

9. A sterile, stable, dry-mix of microcrystalline cisplatin in a sealed container in unit dosage form, reconstitutable with sterile water within about three minutes at a concentration of 1 mg. of microcrystalline cisplatin per ml. of sterile water, and suitable for intravenous administration to man; said dry-mix also containing a customary, harmless, physiologically acceptable excipient in a concentration of from about 2 mgs. to about 150 mgs. per mg. of microcrystalline cisplatin; said microcrystalline cisplatin having a particle size distribution of at least about 80% in the range of 0 to 5 micrometers, less than about 20% in the range of 5 to 20 micrometers and essentially no particles larger than 20 micrometers; the crystalline form of said microcrystalline cisplatin being different from that of lyophilized cisplatin as demonstrable by x-ray powder diffraction patterns.

10. The dry-mix of claim 9 wherein the excipient is mannitol.

11. The dry-mix of claim 10 wherein the mannitol is present at a concentration of about 10 mg. per mg. of microcrystalline cisplatin.

12. A sterile, stable dry-mix of microcrystalline cisplatin in a sealed container in unit dosage form, reconstitutable with sterile water within about three minutes at a concentration of 1 mg. of microcrystalline cisplatin per ml. of sterile water, and suitable for intravenous administration to man; said dry-mix also containing both a sterile, nontoxic, pharmaceutically acceptable, inorganic source of chloride ions in an amount equivalent to that produced by the presence of sodium chloride in a concentration of from about 1 to about 20 mgs. per mg. of microcrystalline cisplatin and a customary, harmless, physiologically acceptable excipient in a concentration of from about 2 mgs. to about 150 mgs. per mg. of microcrystalline cisplatin; said microcrystalline cisplatin having a particle size distribution of at least about 80% in the range of 0 to 5 micrometers, less than about 20% in the range of 5 to 20 micrometers and essentially no particles larger than 20 micrometers; the crystalline form of said microcrystalline cisplatin being different from that of lyophilized cisplatin as demonstrable by x-ray powder diffraction patterns.

13. The dry-mix of claim 12 wherein the inorganic source of chloride ions is sodium chloride and the excipient is mannitol.

14. The dry-mix of claim 13 wherein the sodium chloride is present at a concentration of about 9 mgs. per mg. of microcrystalline cisplatin and the mannitol is present at a concentration of about 10 mgs. per mg. of microcrystalline cisplatin.

15. The dry-mix of claim 6, 7, 8, 9, 10, 11, 12, 13 or 14 wherein the microcrystalline cisplatin has an x-ray powder diffraction pattern substantially as follows:

| Two Theta (Degrees) | Relative Intensity | Interplanar Spacings (Angstroms) |
|---|---|---|
| 13.81 | 100 | 6.407 |
| 14.93 | 84 | 5.929 |
| 16.26 | 71 | 5.447 |
| 24.05 | 27 | 3.697 |
| 26.57 | 22 | 3.352 |
| 28.37 | 16 | 3.143 |
| 30.35 | 13 | 2.943 |
| 33.14 | 15 | 2.701 |

* * * * *